(12) United States Patent
Glenn et al.

(10) Patent No.: US 10,321,999 B2
(45) Date of Patent: Jun. 18, 2019

(54) SYSTEMS AND METHODS FOR RESHAPING A HEART VALVE

(71) Applicant: Millipede, Inc., Santa Rosa, CA (US)

(72) Inventors: Richard Glenn, Santa Rosa, CA (US); Kristian Kristoffersen, Redding, CA (US); Richard Klein, Santa Rosa, CA (US); Randall Lashinski, Windsor, CA (US)

(73) Assignee: Millipede, Inc., Santa Rosa, CA (US)

( * ) Notice: Subject to any disclaimer, the term of this patent is extended or adjusted under 35 U.S.C. 154(b) by 410 days.

(21) Appl. No.: 14/774,656

(22) PCT Filed: Mar. 13, 2014

(86) PCT No.: PCT/US2014/026333
§ 371 (c)(1),
(2) Date: Sep. 10, 2015

(87) PCT Pub. No.: WO2014/160330
PCT Pub. Date: Oct. 2, 2014

(65) Prior Publication Data
US 2016/0038285 A1 Feb. 11, 2016

Related U.S. Application Data

(60) Provisional application No. 61/783,420, filed on Mar. 14, 2013.

(51) Int. Cl.
*A61F 2/24* (2006.01)
(52) U.S. Cl.
CPC .......... *A61F 2/2442* (2013.01); *A61F 2/2445* (2013.01); *A61F 2/2466* (2013.01);
(Continued)

(58) Field of Classification Search
CPC .... A61F 2/2442; A61F 2/2445; A61F 2/2451; A61B 2017/00783; A61B 2017/0641
See application file for complete search history.

(56) References Cited

U.S. PATENT DOCUMENTS

2007/0093869 A1* 4/2007 Bloom ............... A61B 17/0644
606/219
2007/0112423 A1 5/2007 Chu
(Continued)

FOREIGN PATENT DOCUMENTS

EP 2 656 816 10/2013
WO WO 00/07521 2/2000

OTHER PUBLICATIONS

International Search Report and Written Opinion; Application No. PCT/US2014/026333; dated Jul. 21, 2014.

*Primary Examiner* — Sarah W Aleman
(74) *Attorney, Agent, or Firm* — Knobbe Martens Olson & Bear LLP

(57) ABSTRACT

The present disclosure includes a device for reshaping a heart valve. The device may include a central ring about a central axis and a plurality of arms coupled to the central ring, each of the arms coupled to the central ring at a pivot point at a first end of the arm, the arm comprising an attachment feature at a second point along the arm, the pivot point configured to allow movement of the arm about the pivot point through a plane extending radially from the central axis through the arm. Additionally, the plurality of arms may be contractable and may be extendable such that the hooks extend beyond a dilated heart valve. The present disclosure also includes associated methods and systems.

16 Claims, 7 Drawing Sheets

(52) U.S. Cl.
    CPC ............... *A61F 2210/0014* (2013.01); *A61F 2220/0016* (2013.01); *A61F 2220/0091* (2013.01); *A61F 2230/0093* (2013.01)

(56) References Cited

U.S. PATENT DOCUMENTS

2010/0298929 A1   11/2010   Thornton et al.
2011/0202127 A1    8/2011   Mauch et al.

\* cited by examiner

SYSTEMS AND METHODS FOR RESHAPING A HEART VALVE

PRIORITY INFORMATION

The present application claims priority under 35 U.S.C. § 119(e) to U.S. Provisional Patent Application Ser. No. 61/783,420, filed Mar. 14, 2013 and incorporated by reference herein.

TECHNICAL FIELD OF THE INVENTION

The present disclosure relates generally to heart treatment devices and methods, and more particularly, to systems and methods for reshaping a heart valve.

BACKGROUND

The present disclosure addresses heart valve incompetency. For example, heart disease can cause the chambers of the heart to expand and weaken. With specific reference to the mitral valve, as the left ventricle dilates, the papillary muscles are displaced. Consequently, the annulus of the mitral heart valve dilates, excessively. In this state of dilation, valve leaflets no longer effectively close, or coapt, during systolic contraction. Consequently, regurgitation of blood occurs during ventricular contraction and cardiac output is decreased.

This condition is typically addressed by open-heart surgical implantation of an annuloplasty ring. A surgeon positions the annuloplasty ring proximate the valve annulus and sutures it in place thereby restoring the valve annulus to approximately its native circumference. The valve leaflets can then function normally again.

SUMMARY

In one embodiment, the present disclosure includes a device for reshaping a heart valve comprising a central ring about a central axis and a plurality of arms coupled to the central ring, each of the arms coupled to the central ring at a pivot point at a first end of the arm, the arm comprising an attachment feature at a second point along the arm, the pivot point configured to allow movement of the arm about the pivot point through a plane extending radially from the central axis through the arm. In this embodiment, the plurality of arms are contractable and are extendable such that the attachment features extend beyond a dilated heart valve.

In another embodiment, the present disclosure includes a method for reshaping a heart valve comprising deploying a device, the device comprising a central ring about a central axis and a plurality of arms coupled to the central ring, each of the arms coupled to the central ring at a pivot point at a first end of the arm, the arm comprising an attachment feature at a second point along the arm, the pivot point configured to allow movement of the arm about the pivot point through a plane extending radially from the central axis through the arm. The method also includes extending the plurality of arms beyond a dilated heart valve and engaging the attachment features into tissue proximate the dilated heart valve. The method additionally includes contracting the plurality of arms to reduce the circumference of the dilated heart valve.

In an additional embodiment, the present disclosure includes a system comprising a delivery catheter and a delivery shaft disposed within the delivery catheter. The system also includes a device for delivery by the delivery catheter and removably coupled to the delivery shaft. The device comprises a central ring about a central axis, and a plurality of arms coupled to the central ring, each of the arms coupled to the central ring at a pivot point at a first end of the arm, the arm comprising an attachment feature at a second point along the arm, the pivot point configured to allow movement of the arm about the pivot point through a plane extending radially from the central axis through the arm. In such an embodiment, the plurality of arms are contractable and are extendable such that the attachment features extend beyond a dilated heart valve.

BRIEF DESCRIPTION OF THE DRAWINGS

For a more complete understanding of the present disclosure and its features and advantages, reference is now made to the following description, taken in conjunction with the accompanying drawings, in which.

DETAILED DESCRIPTION

The present disclosure addresses systems and methods for reshaping a heart valve. A device with a plurality of arms coupled to a central ring may be utilized to reshape a heart valve. The device may pivot about one end of the arms, which may be coupled to the central ring. At a second point along a respective arm (for example, the opposite end from the pivot point), there may be a hook or some other attachment feature. An arm may have its pivoting motion limited to the plane extending radially from a central axis of the ring through the arm. The device may also include a slider with linkages between the slider and the arms. Thus, the action of the device may resemble that of a parasol as the slider is slid along the central axis of the central ring to cause the arms of the device to extend or contract. To reshape the heart valve, the device may be deployed proximate the valve annulus. The arms may be extended (for example, like a parasol opening) beyond the annulus or beyond a diseased or dilated heart valve and then the hooks at the end of the arms may be engaged with the tissue, for example, by pulling the device down against the valve with the arms extended. Once the hooks are engaged, the arms may be contracted (for example, like a parasol closing). With the hooks engaged in the tissue, the contracting arms may draw the annular tissue inwards as they are contracted such that the valve leaflets coapt more appropriately by decreasing the circumference of the valve annulus or the area of the valve opening. The device may then be caused to retain its contracted shape.

Figure 1A:
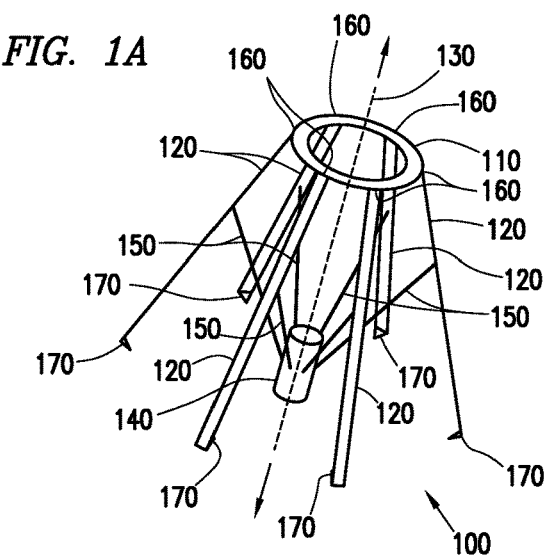
FIGS. 1A through 1D illustrate an example of a device for reshaping a heart valve, in accordance with some embodiments of the present disclosure.
Figure 1B:
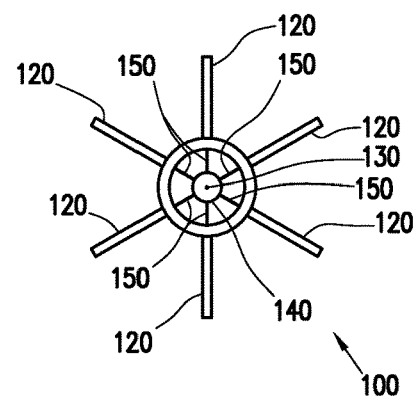

FIGS. 1A and 1B illustrate an example of a device 100 for reshaping a heart valve, in accordance with some embodiments of the present disclosure. FIG. 1A illustrates a perspective view and FIG. 1B illustrates a top-down view of device 100. Device 100 may include a central ring 110 with a plurality of arms 120 coupled to central ring 110. For reference, a central axis 130 may pass through the center of central ring 110 and be perpendicular to the plane of central ring 110. Device 100 may further include a slider 140, which is slidable along central axis 130 and linkages 150, which are coupled to slider 140 and to arms 120. Device 100 may be made of any suitable biocompatible metal or high strength polymer such as stainless steel, cobalt chromium, nitinol, titanium, platinum, platinum/iridium, high molecular weight polyethylene or polyurethane, or any other biocompatible material as is known in the art.

Each arm 120 may be coupled to central ring 110 at a pivot point 160. Device 100 may be expanded or contracted by extending or contracting arms 120 about their respective pivot points 160. In some embodiments, the motion of arms 120 may be limited to essentially motion along the plane extending radially from central axis 130 to a particular arm 120. For example, the coupling between a given arm 120 and central ring 110 may limit this motion as the coupling may be a hinge, an eye socket on arm 120 at pivot point 160, or some other mechanism as known in the art to facilitate motion limited about a pivot point. The motion of each arm may be independent, or some or all of the arms may be moved simultaneously.

The motion of extending or contracting arms 120 about pivot point 160 may be facilitated using slider 140 and linkages 150. By way of example, when slider 140 is at a position away from central ring 110, arms 120 may be in a more contracted position. When slider 140 is slid along central axis 130 from an initial position away from central ring 110 and towards central ring 110, linkages 150 may push arms 120 radially outward from central axis 130, extending arms 120 of device 100. In the reverse, when slider 140 is slid along central axis 130 from a position proximate central ring 110 away from central ring 110, linkages 150 may pull arms 120 in towards central axis 130, contracting arms 120 of device 100. By way of example and in no way meant to be limiting, this motion using slider 140 and linkages 150 may be similar conceptually to that observed in a parasol in which a slider may be used to open and close the parasol. In some embodiments, linkages 150 may comprise more than one piece. For example, linkages 150 may include two components that are coupled by a hinge joint, or two components that slide past each other.

Figure 1C:
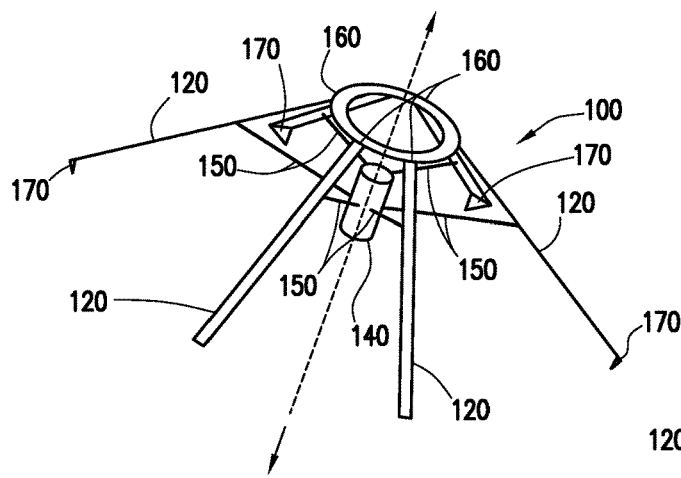
Figure 1D:
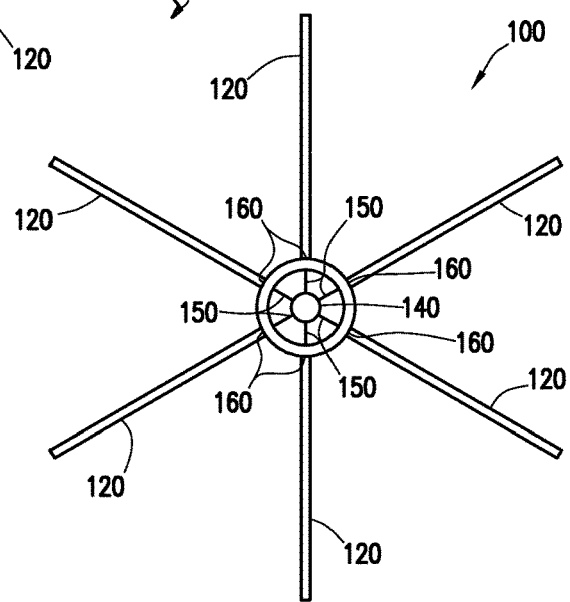

FIGS. 1C and 1D illustrate an example perspective view (FIG. 1C) and top-down view (FIG. 1D) of device 100 when its arms 120 are extended. As shown in FIGS. 1C and 1D, as slider 140 is moved closer to central ring 110, linkages 150 may force arms 120 to extend radially outward from central ring 110.

In some embodiments, linkages 150 may include a hinge joint at each end. In other words, linkage may have a hinge at both slider 140 and arm 120. Linkages 150 may also simply rely on the flexion of a rigid body to accomplish the parasol-like motion of arms 120. For example, if linkages 150 are fixed to slider 140 and unattached to arms 120, as slider 140 is moved closer to central ring 110, linkages 150 may force arms 120 to extend. If arms 120 were biased towards a closed position (for example using springs or a memory shaped material) or if arms 120 are coupled to linkage 150 with a hinge joint, when slider 140 is moved away from central ring 110, arms 120 would contract. It will be appreciated that these are merely examples of implementations of the parasol-like motion, and any similar expansion or contraction supported by a slider and linkages would be within the scope of the present disclosure.

On the opposite end of arms 120 from pivot point 160 may be one or more hooks 170. Hooks 170 may be designed and shaped to pierce and engage annular tissue. In some embodiments, hooks 170 may be a tapered point of arm 120. Hooks 170 may also be an angled and tapered point of arm 120. For example, hooks 170 may be angled at between approximately forty-five degrees and ninety degrees relative to the annular tissue when arms 120 are fully extended, although these are merely examples and any angle that facilitates hooks 170 piercing and engaging the annular tissue would be within the present disclosure. The angled orientation of hooks 170 to the annular heart tissue may reduce the force needed to pierce the annular tissue.

As will be appreciated, as device 100 is contracted by contracting arms 112, the orientation of hooks 170 may also change. As their orientation changes, hooks 170 may transition from perpendicular to the annular tissue to facilitate piercing the tissue, to an angled orientation for scooping tissue or drawing tissue towards central axis 130. This inward orientation may be angled such that it opposes the forces and movement of the surrounding annular tissue and heart structures. In some embodiments, hooks 170 may be oriented differently with respect to each other such that, overall, they are resisting forces, in multiple vectors, that might tend to extract or dislodge hooks 170. This may be beneficial due to the continuous beating of the heart, generating diverse directions of forces on device 100, which might otherwise dislodge device 100.

Figure 2A:
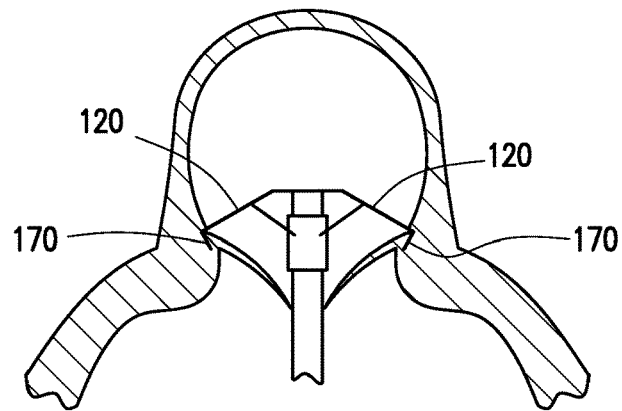
FIGS. 2A and 2B illustrate an example embodiment of reshaping a heart valve using a device, in accordance with some embodiments of the present disclosure.
Figure 2B:
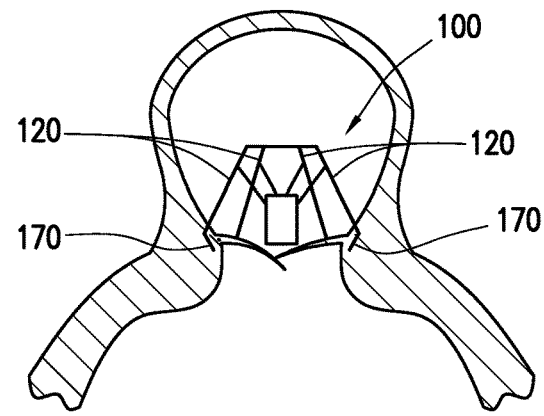

FIGS. 2A and 2B illustrate an example embodiment of reshaping a heart valve using a device, in accordance with some embodiments of the present disclosure. FIGS. 2A and 2B will be described with reference to device 100 of FIGS. 1A-1D. Once device 100 has been deployed to a desired location, for example, a left atrium with a dilated valve, device 100 may be expanded by extending arms 120 of device 100. As described above and by way of non-limiting example, this motion may be analogous to a parasol opening. Once extended beyond the dilated valve annulus, a force may be applied to engage hooks 170 with the annular tissue. For example, as shown in FIG. 2A, device 100 has hooks 170 which have been engaged in annular tissue.

With hooks 170 engaged in annular tissue, device 100 may be contracted such that hooks 170 draw the annular tissue with them to reduce the circumference or area of the valve opening. This may, for example, reduce or lessen mitral regurgitation. As described above and by way of non-limiting example, this motion may be analogous to a parasol closing. For example, as shown in FIG. 2B, hooks 170 are engaged with the tissue and arms 120 have contracted, drawing the valve leaflets closer together. The action of hooks 170 when contracting arms 120 may also be described as gathering or pushing the heart tissue surrounding the valve inwardly. The circumference of the annulus or valve area may thus be reduced such that the valve leaflets coapt normally and regurgitation is reduced. In some embodiments, regurgitation may be completely eliminated.

Figure 3:
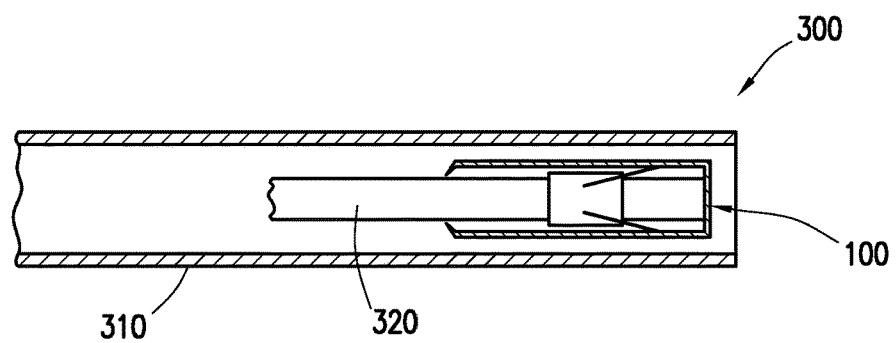
FIG. 3 illustrates an example of a delivery system for delivery of a device for reshaping a valve, in accordance with some embodiments of the present disclosure.

FIG. 3 illustrates an example of a delivery system for delivery of a device for reshaping a valve. As shown in FIG.

3, a delivery system 300 may include a delivery catheter 310, a delivery shaft 320, and a device 100 for reshaping a valve.

Delivery catheter 310 may be any catheter with sufficient circumference to carry device 100 and delivery shaft 320. Delivery catheter 310 may be introduced using any known method or route to arrive at the desired chamber of the heart. For example, delivery catheter 310 may be routed transapically, transseptally from the right atrium, or through the femoral artery over the aortic arch and through the left ventricle. Still another entry may be directed through the left atrium.

Delivery shaft 320 may be removably coupled to device 100. For example, after deployment in the heart tissue and retraction of device 100, delivery shaft 320 may be decoupled from device 100, for example, by disengaging or unthreading, leaving device 100 behind as a permanent implant. Device 100 thus may also include corresponding threads, couplings, sockets, or other connecting features to allow device 100 to be removably coupled with delivery shaft 320.

A typical delivery process may include using a guidewire to navigate the body as described above to the desired chamber of the heart, for example, the left atrium. Delivery catheter 310 may then be fed down the guidewire to the desired chamber. Delivery shaft 320 may then be guided down delivery catheter 310 and into the desired chamber either passively by the guidewire or actively by steering means from outside the patient via control handle. The controls may include push-pull wire mechanism and or rotational controls or the catheters or sheaths for accurate delivery. At this point, delivery catheter 310 may be partially withdrawn or delivery shaft 320 may be extended beyond delivery catheter 310 such that device 100 is no longer constrained within delivery catheter 310.

Figure 4A:
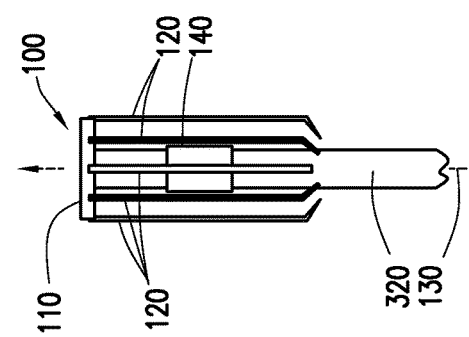
FIGS. 4A-4F illustrate an example of expanding a device, in accordance with some embodiments of the present disclosure.
Figure 4B:
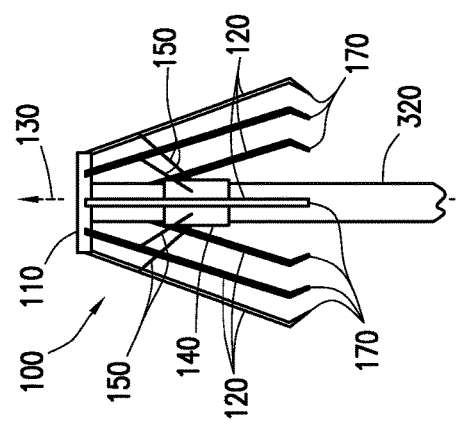
Figure 4C:
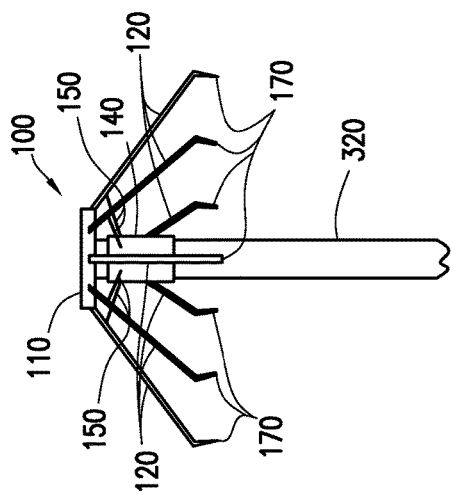
Figure 4D:
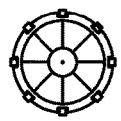
Figure 4E:
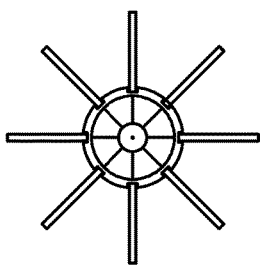
Figure 4F:
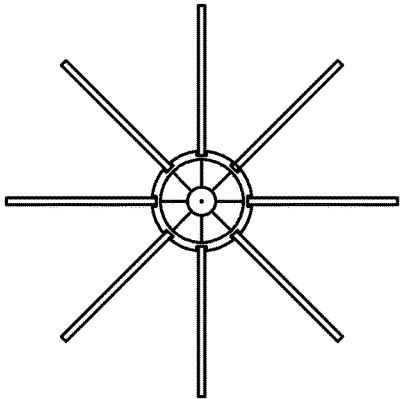

FIGS. 4A-4C illustrate a side view of an example of expanding a device, and FIGS. 4D-4F illustrate corresponding top views of an example of expanding a device, in accordance with some embodiments of the present disclosure. With reference to FIGS. 4A-4F, once no longer constrained within delivery catheter 310 shown in FIG. 3, device 100 may be expanded by extending arms 120 of device 100. This may be accomplished, for example, by sliding slider 140 along central axis 130 from a location at its maximum distance from central ring 110 (for example as shown in FIGS. 4A and 4D) to a position proximate central ring 110 (for example progressing from the positions shown in FIGS. 4A and 4D to that shown in FIGS. 4B and 4E and ultimately to that shown in FIGS. 4C and 4F). Slider 140 may be configured to slide along delivery shaft 320. This may be done by a tool within delivery catheter 310 able to move relative to delivery shaft 320 to force slider 140 along delivery shaft 320. As described above and by way of non-limiting example, this motion may be analogous to a parasol opening.

Once expanded beyond a dilated valve annulus, a force may be applied via the delivery shaft 320 to engage hooks 170 with the annular tissue. Once engaged, device 100 may be contracted, hooks 170 drawing the annular tissue with them to reduce the circumference of the valve. This may be accomplished, for example, by sliding slider 140 along central axis 130 from a location proximate central ring 110 (for example, as shown in FIGS. 4C and 4F) to a location further away from central ring 110 (for example, that shown in FIGS. 4B and 4E). This may be done by sliding slider 140 along delivery shaft 320. As described above and by way of non-limiting example, this motion may be analogous to a parasol closing.

Depending on the delivery path, delivery catheter 310 may be approaching the valve from above the valve (e.g. from within the atrium) or may be approaching the valve from beneath the valve (e.g. from within the ventricle, through the valve and into the atrium). When approaching from above the valve, a force may be generated to engage hooks 170 with the annular tissue by pushing on delivery shaft 320. This may then be pushing device 100 and thus hooks 170 into the annular tissue. When approaching from below the valve, a force may be generated to engage hooks 170 with the annular tissue by pulling on delivery shaft 320. This may then pull device 100 and thus hooks 170 into the annular tissue.

Figure 5A:
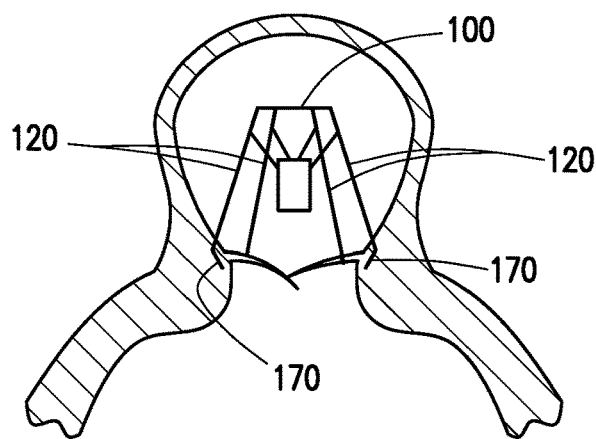
FIGS. 5A and 5B illustrate an example of utilizing an engaging member, in accordance with some embodiments of the present disclosure.
Figure 5B:
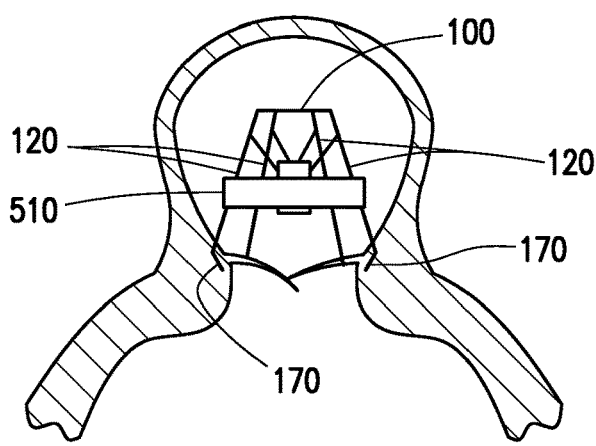

FIGS. 5A and 5B illustrate an example of utilizing an engaging member, in accordance with some embodiments of the present disclosure. For example, FIG. 5A illustrates device 100 with hooks 170 engaged with annular tissue. Further, as shown in FIG. 5A, arms 120 are contracted down a certain amount such that the circumference of the valve has been reduced. In some embodiments of the present disclosure, an engaging member may be utilized to prevent arms 120 from extending beyond a desired size. The present disclosure contemplates any mechanism employed or component coupled to device 100 to maintain arms 120 in a contracted state. One non-limiting, illustrative example of such an engaging member is a ring like that illustrated in FIG. 5B.

FIG. 5B illustrates a ring 510 that may be slid over the top of device 100 to engage arms 120 to maintain device 100 in the contracted state. By maintaining arms 120 of device 100 in a contracted state, the dilated valve may also be maintained in a reduced circumference. Placing ring 510 over the top of device 100 and sliding it down arms 120 of device 100 may further contract arms 120 by applying a force to the outside of arms 120, where slider 140 and linkages 150 of FIGS. 1A-1D applied a force to the inside of arms 120. In some embodiments, arms 120 may have a groove or notch on the outside for ring 510 to settle in once ring 510 has been slid down the outside of arms 120 a desired distance. Ring 510 may be made of any biocompatible material, for example, metal, metal alloy, plastic, elastomer, or other biocompatible materials as known in the art. In addition to ring 510, other engaging members may be used to maintain arms 120 of device 100 in a contracted state.

Figure 6A:
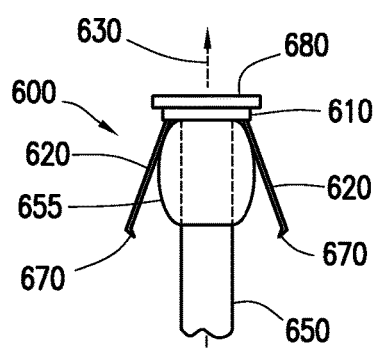
FIGS. 6A-6D illustrate an example embodiment of a device for reshaping a heart valve.

FIGS. 6A-6D illustrate an example embodiment of a device 600 for reshaping a heart valve. As shown in FIG. 6A, in some embodiments, device 600 may include a central ring 610, arms 620 coupled to central ring 610, and hooks 670 at the end of arms 620. For reference, a central axis 630 may pass through the center of central ring 610 and be perpendicular to the plane of central ring 610. In the embodiment shown in FIGS. 6A-6D, an alternative mechanism is used to extend and contract arms 620 of device 600 when compared with the mechanism described with respect to FIGS. 1A-1D. While arms 620 follow a similar path of motion as that described with respect to device 100 of FIGS. 1A-1D, device 600 does not use a slider or linkage system similar to that illustrated in FIGS. 1A-1D. For example, the motion of arms 620 may be limited to essentially motion along the plane extending radially from central axis 630 to a particular arm 620.

In some embodiments, the force to contract arms 620 may be derived by using a shape memory material, for example nitinol. For example, device 600 may have a memory configuration of a contracted state such that device 600 may be deployed or deformed to a particular state and, at body temperature, will transform back to the contracted state. This may be a completely contracted state, for example one in which arms 620 are substantially parallel with central axis 630, or may be only partially contracted, for example one in which arms 620 are at some acute angle (for example between zero and sixty degrees) with central axis 630.

To provide the expansive force to extend arms 620 of device 600, a delivery catheter 650 may utilize a balloon 652. For example, when deploying device 600, balloon 652 may be disposed between arms 620 and delivery shaft 650. When device 600 has been disposed within the desired location (e.g. the left atrium), balloon 652 may be inflated to cause arms 620 to extend outward against the inwardly biased memory shape of device 600. For example, when comparing FIG. 6A to FIG. 6B, balloon 655 is inflated causing arms 620 to be extended.

In some embodiments, the expansion caused by inflation of balloon 655 may not be only about the point where arms 620 couple with central ring 610. For example, a portion of the displacement of arms 620 caused by balloon 655 may be bowing or bending of arms 620.

In some embodiments, a cap 680 may be used to limit the expansion of arms 620 based on the inflation of balloon 652. For example, cap 680 may prevent arms 620 from extending beyond approximately perpendicular to central axis 630. Cap 680 may be part of device 600 or may be a separate component that may be deployed with delivery shaft 650 and removed upon contraction of arms 620.

Figure 6B:
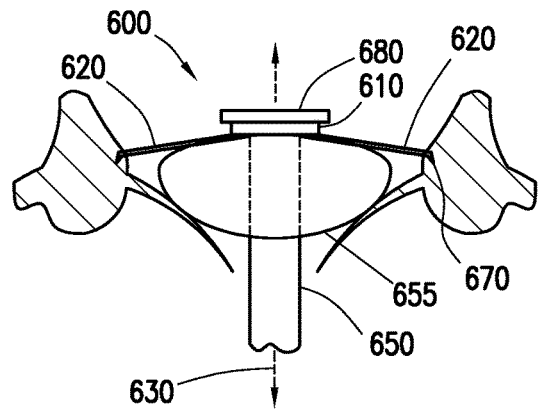
Figure 6C:
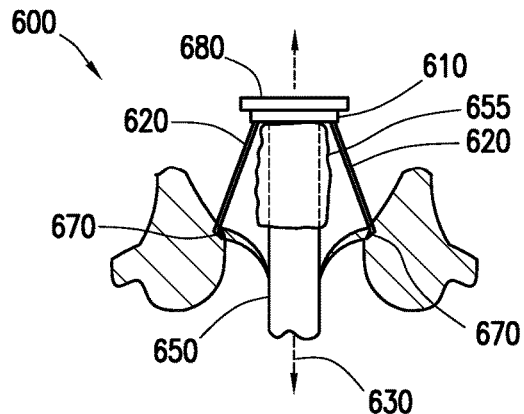

With this embodiment in mind, as shown in FIG. 6B, balloon 655 may be inflated to extend arms 620 beyond their shape memory state. In this extended state, a force may be applied to cause hooks 670 to engage the annular tissue. As shown in FIG. 6C, once the hooks have engaged the annular tissue, balloon 655 may be deflated. As balloon 655 is deflated the shape memory characteristics of device 600 cause arms 620 to contract back to their shape memory state. As this occurs, hooks 670, which are engaged in the annular tissue, draw the annular tissue along with them causing a decrease in the circumference of the valve. Stated another way, as arms 620 contract back to their shape memory state, hooks 670 gather or push the heart tissue surrounding the annulus or valve area inwardly.

Figure 6D:
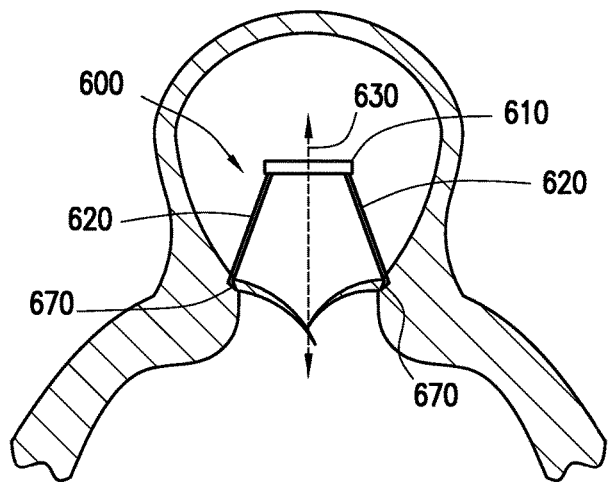

Once balloon 655 has been sufficiently deflated, delivery shaft 650 and balloon 655 may be withdrawn such that device 600 remains as a permanent implant to maintain the reduced circumference of the heart valve. In embodiments where cap 680 is a separate component, it may also be retrieved and withdrawn at the same time that delivery shaft 650 and balloon 655 are withdrawn. This may leave device 600 in a final configuration as a permanent implant, for example, as shown in FIG. 6D.

In some embodiments, central ring 610 and arms 620 may be a unitary body of shape memory material. Alternatively, arms 620 may be shape memory material and coupled to central ring 610 as a separate component. In some embodiments, multiple arms 620 may be a unitary body coupled to central ring 610.

The embodiments shown in FIGS. 6A-6D may also use an engaging member to provide assistance to device 600 in returning to its contracted memory shape and/or in retaining its contracted shape. For example, a ring may be placed over the top of device 600 and slid down arms 620, providing additional force to contract arms 620.

In some embodiments the devices for reshaping a heart valve of the present disclosure may also be covered in Dacron, polyester, or some other biocompatible material. It may be that only a portion of the device may be covered, for example, any one or combination of the arms, central ring, linkages, hooks, and slider may be covered.

Figure 7A:
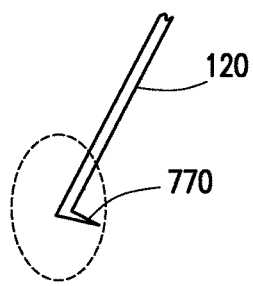
FIGS. 7A-7D illustrate an example of operation of an example hook, in accordance with some embodiments of the present disclosure.
Figure 7B:
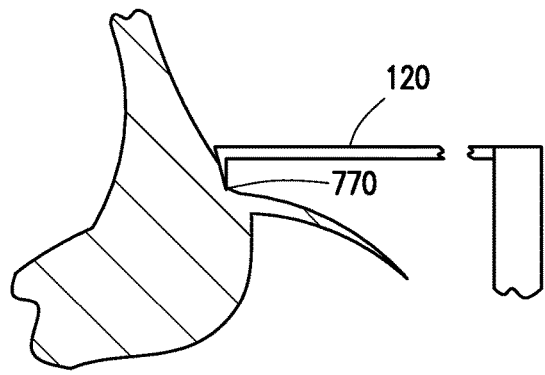

FIGS. 7A-7D illustrate an example of operation of an example hook, in accordance with some embodiments of the present disclosure. As shown in FIG. 7A and as described above, at the end of arm 120 is a hook 770. As shown in FIG. 7A, the profile of hook 770 may be a tapered point of arm 120. Additionally, as shown in FIG. 7B, hook 770 may be angled such that it is positioned to more effectively pierce, penetrate, or otherwise engage annular tissue. For example, as described above, hook 770 may form an angle of between approximately forty-five and ninety degrees with the annular tissue.

Figure 7C:
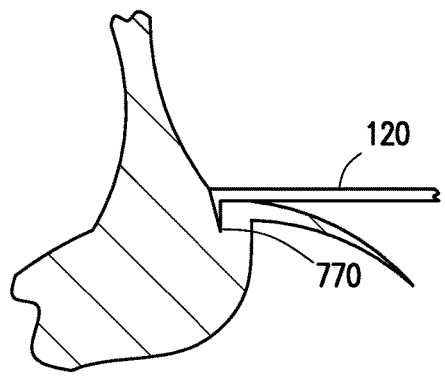
Figure 7D:
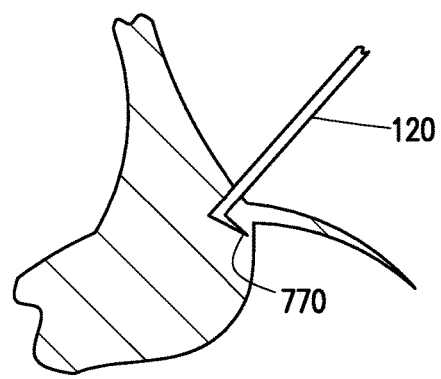

As illustrated between FIGS. 7B and 7C, a force may be applied to cause hook 770 to pierce, penetrate, or otherwise engage the annular tissue. Once that has occurred, arm 120 may be contracted, as described herein. As illustrated in FIG. 7D, as arm 120 is contracted, hook 770 gathers and draws annular tissue inward with it as arm 120 contracts. Additionally, because of the orientation of hook 770, it may resist withdrawal from the annular tissue, with the resistance increasing the further arm 120 is contracted.

Figure 8A:
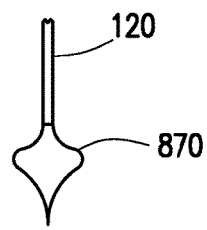
FIGS. 8A-8D illustrate an example of operation of another example hook, in accordance with some embodiments of the present disclosure.
Figure 8B:
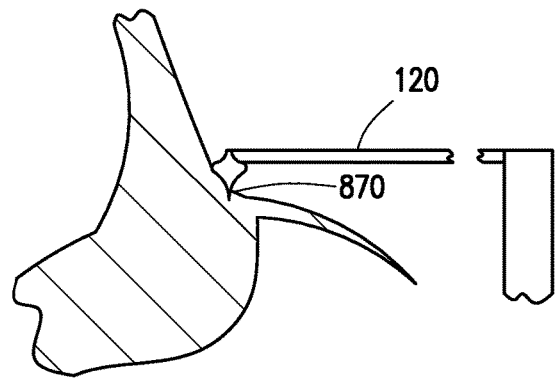
Figure 8C:
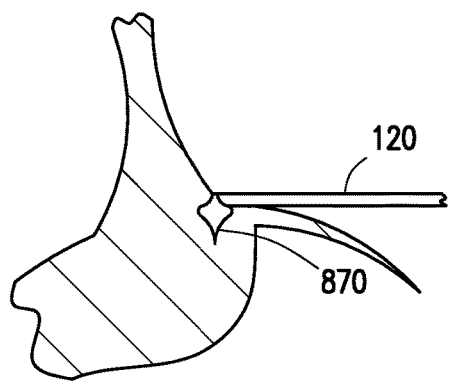
Figure 8D:
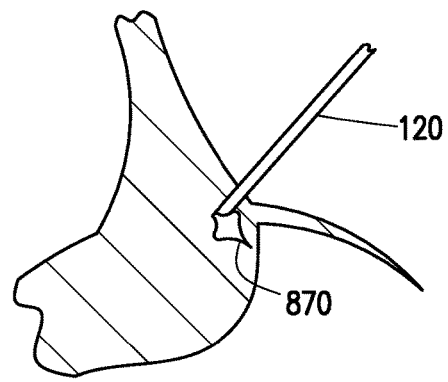

FIGS. 8A-8D illustrate an example of operation of another example hook, in accordance with some embodiments of the present disclosure. As shown in FIG. 8A, at the end of arm 120 is a hook 870. As shown in FIG. 8A, the profile of hook 870 may include a point but may also include scoops on either side of the point. In other words, hook 870 may have a scooped profile. These scoops may be shaped such that hook 870 may still be able to adequately puncture, pierce, or otherwise engage annular tissue. For example, hook 870 may be flat but with the profile shown in FIG. 8. In this way, for example as shown in FIGS. 8B and 8C, arm 120 may be extended and then hook 870 may be forced into the annular tissue. As shown in comparison of FIGS. 8C to 8D, as arm 120 is contracted, hook 870 is able to draw annular tissue inwards with it. When compared to the profile of hook 770 illustrated in FIG. 7A, the profile of hook 870 of FIG. 8A may have an increased surface area to catch and draw more annular tissue inwards as arm 120 contracts. This may be because of the scoops on either side of the point of hook 870.

While two examples of hooks are shown in FIGS. 7A-7D and FIGS. 8A-8D, it will be appreciated that the hooks of the present disclosure could take any of a variety of profiles or shapes and are within the scope of the present disclosure. For example, as the surface area of a hook is increased, it will resist contraction of the arm more but will draw more annular tissue inwards with it. An increase in surface area may also make it more difficult for the hook to pierce the annular tissue. As the surface area decreases, or in other words, as the point becomes more pointed, it may become easier to pierce the annular tissue. However, this may come at a cost that the hook may not draw as much annular tissue with it when the hook's arm contracts.

Additionally, the hooks of the present disclosure may include features to resist withdrawal from the annular tissue. For example, they may include barbs, protrusions, or other projections that prevent or resist withdrawal of the hooks out of the annular tissue. In some embodiments, a portion of the hooks may be sharpened or otherwise configured to more readily pierce or engage with the annular tissue.

In addition to the profiles of hooks shown in FIGS. 7A-7D and FIGS. 8A-8D, other attachment feature may be used to engage the arms with the tissue. By way of non-limiting example, this may include staples, sutures, or barbs to engage the tissue proximate the heart valve.

While hooks 170, hooks 770 and hooks 870 are all shown at an end of the plurality of arms, it is envisioned that an attachment feature, including said hooks, could be placed at any point along a respective arm. For example, the feature may be placed near the end opposite the pivot point, but not all the way to the end. As another example, the attachment feature may be located approximately half way down the arm. In some embodiments, more than one hook or other attachment feature may be included on an arm, and may be at more than one location.

This disclosure encompasses all changes, substitutions, variations, alterations, and modifications to the example embodiments herein that a person having ordinary skill in the art would comprehend. Similarly, where appropriate, the appended claims encompass all changes, substitutions, variations, alterations, and modifications to the example embodiments herein that a person having ordinary skill in the art would comprehend. Moreover, reference in the appended claims to an apparatus or system or a component of an apparatus or system being adapted to, arranged to, capable of, configured to, enabled to, operable to, or operative to perform a particular function encompasses that apparatus, system, component, whether or not it or that particular function is activated, turned on, or unlocked, as long as that apparatus, system, or component is so adapted, arranged, capable, configured, enabled, operable, or operative. For example, various embodiments may perform all, some, or none of the steps described above. Various embodiments may also perform the functions described in various orders.

Although the present invention has been described above in connection with several embodiments; changes, substitutions, variations, alterations, transformations, and modifications may be suggested to one skilled in the art, and it is intended that the present invention encompass such changes, substitutions, variations, alterations, transformations, and modifications as fall within the spirit and scope of the appended claims.

What is claimed is:

1. A device for reshaping a heart valve comprising:
   a central ring about a central axis;
   a plurality of arms coupled to the central ring, each of the arms coupled to the central ring at a pivot point at a first end of the arm, the arm comprising an attachment feature at a second point along the arm, the pivot point configured to allow movement of the arm about the pivot point through a plane extending radially from the central axis through the arm;
   a slider slidable along the central axis relative to the central ring;
   a plurality of linkages, each of the plurality of linkages coupled to the slider and coupled to a respective arm of the plurality of arms to facilitate the movement of the plurality of arms,
   wherein the plurality of arms are contractable and are extendable such that the attachment feature extends beyond a dilated heart valve; and
   an engaging member to maintain the plurality of arms in a contracted state, wherein the engaging member comprises a cover ring configured to slide over the plurality of arms to prevent their extension beyond the cover ring, and wherein an outside of the arms have a groove or notch for the cover ring to settle in once the cover ring has slid down the outside of the arms a desired distance.

2. The device of claim 1, further comprising a cap to prevent the plurality of arms from extending beyond approximately ninety degrees with the central axis.

3. The device of claim 1, wherein the central ring is a unitary body with the plurality of arms.

4. The device of claim 3, wherein the device is made of a shape memory material and the plurality of arms contract due to the shape memory material of the device.

5. The device of claim 1, wherein at least two of the attachment features are oriented differently with respect to each other such that different force vectors are resisted by the at least two attachment features.

6. The device of claim 1, wherein the attachment feature is a hook with a scooped profile.

7. The device of claim 1, wherein the plurality of arms are contractable such that the plurality of arms are substantially parallel with the central axis.

8. The device of claim 1, wherein at least a portion of the device is covered with a biocompatible material.

9. A method for reshaping a heart valve comprising:
   deploying a device comprising:
      a central ring about a central axis;
      a plurality of arms coupled to the central ring, each of the arms coupled to the central ring at a pivot point at a first end of the arm, the arm comprising an attachment feature at a second point along the arm, the pivot point configured to allow movement of the arm about the pivot point through a plane extending radially from the central axis through the arm;
      a slider slidable along the central axis relative to the central ring;
      a plurality of linkages, each of the plurality of linkages coupled to the slider and coupled to a respective arm of the plurality of arms to facilitate the movement of the plurality of arms; and
      an engaging member to maintain the plurality of arms in a contracted state, wherein the engaging member comprises a cover ring configured to slide over the plurality of arms to prevent their extension beyond the cover ring, and wherein an outside of the arms have a groove or notch for the cover ring to settle in once the cover ring has slid down the outside of the arms a desired distance,
   extending the plurality of arms beyond a dilated heart valve;
   engaging the attachment features into tissue proximate the dilated heart valve; and
   contracting the plurality of arms to reduce the circumference of the dilated heart valve.

10. The method of claim 9, wherein the device is deployed using a catheter.

11. The method of claim 9, wherein extending the plurality of arms beyond a dilated heart valve comprises sliding the slider towards the central ring.

12. The method of claim 9, wherein contracting the plurality of arms comprises sliding the slider away from the central ring.

13. The method of claim 9, further comprising maintaining the plurality of arms in a contracted state.

14. The method of claim 9, wherein engaging the attachment features is performed by applying a pulling force substantially parallel with the central axis from beneath the dilated heart valve.

15. The method of claim 9, wherein engaging the attachment features is performed by applying a pushing force substantially parallel with the central axis from above the dilated heart valve.

16. A system comprising:

a delivery catheter;

a delivery shaft disposed within the delivery catheter; and a device for delivery by the delivery catheter and removably coupled to the delivery shaft, the device comprising:

a central ring about a central axis;

a plurality of arms coupled to the central ring, each of the arms coupled to the central ring at a pivot point at a first end of the arm, the arm comprising an attachment feature at a second point along the arm, the pivot point configured to allow movement of the arm about the pivot point through a plane extending radially from the central axis through the arm;

a slider slidable along the central axis relative to the central ring;

a plurality of linkages, each of the plurality of linkages coupled to the slider and coupled to a respective arm of the plurality of arms to facilitate the movement of the plurality of arms, wherein the plurality of arms are contractable and are extendable such that the attachment feature extends beyond a dilated heart valve; and an engaging member to maintain the plurality of arms in a contracted state, wherein the engaging member comprises a cover ring configured to slide over the plurality of arms to prevent their extension beyond the cover ring, and wherein an outside of the arms have a groove or notch for the cover ring to settle in once the cover ring has slid down the outside of the arms a desired distance.

* * * * *